(12) United States Patent
Rabkin

(10) Patent No.: US 11,344,467 B2
(45) Date of Patent: May 31, 2022

(54) APPARATUS AND SYSTEMS FOR POWERING SUPPORTS FOR EXOSKELETONS

(71) Applicant: ReWalk Robotics LTD., Yokneam (IL)

(72) Inventor: Roman Rabkin, Haifa (IL)

(73) Assignee: ReWalk Robotics LTD., Yokneam (IL)

( * ) Notice: Subject to any disclaimer, the term of this patent is extended or adjusted under 35 U.S.C. 154(b) by 910 days.

(21) Appl. No.: 15/780,917

(22) PCT Filed: Dec. 4, 2016

(86) PCT No.: PCT/IL2016/051296
§ 371 (c)(1),
(2) Date: Jun. 1, 2018

(87) PCT Pub. No.: WO2017/094018
PCT Pub. Date: Jun. 8, 2017

(65) Prior Publication Data
US 2020/0281802 A1  Sep. 10, 2020

Related U.S. Application Data

(60) Provisional application No. 62/263,468, filed on Dec. 4, 2015.

(51) Int. Cl.
*A61H 3/02* (2006.01)
*H02J 50/10* (2016.01)
(Continued)

(52) U.S. Cl.
CPC .............. *A61H 3/02* (2013.01); *H02J 7/0044* (2013.01); *H02J 7/0048* (2020.01); *H02J 50/10* (2016.02); *H02J 50/60* (2016.02)

(58) Field of Classification Search
CPC ................... A61H 3/02; A61H 3/0244; A61H 2003/0255; A61H 2003/0261;
(Continued)

(56) References Cited

U.S. PATENT DOCUMENTS 7,153,242 B2  12/2006 Goffer
8,905,955 B2  12/2014 Goffer
(Continued)

FOREIGN PATENT DOCUMENTS

DE        3903525       8/1990
JP        2006/014990   1/2006
(Continued)

OTHER PUBLICATIONS

"How do electric toothbrushes charge through plastic?", Planet Science, Nov. 16, 2012, retrieved from Internet Apr. 30, 2021, http://www.planet-science.com/categories/under-11s/our-world/2011/07/how-do-electric-toothbrushes-charge-through-plastic.aspx, entire document. (Year: 2012).*

(Continued)

*Primary Examiner* — Hal Kaplan
(74) *Attorney, Agent, or Firm* — Cooley LLP

(57) ABSTRACT

Some embodiments of the present disclosure are directed to a charging apparatus for charging and/or powering a smart or powered crutch device. The crutch may include electronic circuitry as well as on board rechargeable power or energy source, and it may provide access to charge the power source using a charger system. The charger system may be a floor charger configured to receive a portion of the crutch such as the distal tip so as to facilitate the transfer of power from the charger to the crutch. The charger system may also be in the form of a wall charger and/or a portable system.

17 Claims, 4 Drawing Sheets

(51) Int. Cl.
*H02J 50/60* (2016.01)
*H02J 7/00* (2006.01)

(58) Field of Classification Search
CPC .. A61H 2003/0266; H02J 50/10; H02J 50/60; H02J 7/0044; H02J 7/0048
USPC .......................................................... 135/68
See application file for complete search history.

(56) References Cited

U.S. PATENT DOCUMENTS

| | | |
|---|---|---|
| 2007/0000531 A1 | 1/2007 | Russo |
| 2012/0101415 A1 | 4/2012 | Goffer et al. |
| 2012/0170323 A1* | 7/2012 | Iida .................. H02J 50/12 363/16 |
| 2013/0197408 A1 | 8/2013 | Goldfarb et al. |
| 2013/0253385 A1 | 9/2013 | Goffer et al. |
| 2014/0005577 A1 | 1/2014 | Goffer et al. |
| 2014/0196757 A1 | 7/2014 | Goffer |
| 2014/0358290 A1* | 12/2014 | Kazerooni ............... A61F 4/00 700/275 |
| 2015/0257966 A1* | 9/2015 | Summit .................. A61H 3/02 135/68 |
| 2018/0257216 A1 | 9/2018 | Shavit |
| 2018/0296426 A1 | 10/2018 | Kappel |

FOREIGN PATENT DOCUMENTS

| | | | |
|---|---|---|---|
| JP | 2006014990 A | * | 1/2006 |
| WO | WO-2015102542 A1 | * | 7/2015 ............. F16B 47/00 |

OTHER PUBLICATIONS

"How do electric toothbrushes charge through plastic?" (Planet Science) Nov. 16, 2012 (Nov. 16, 2012); retrieved from internet Apr. 19, 2017; <url= http://www.planet-science.com/categories/under-11s/our-world/2011/07/how-do-electric-toothbrushes-charge-through-plastic.aspx>; entire document, especially Diagram.
International Search Report and Written Opinion dated Jun. 2, 2017, for International Application No. PCT/IL2016/051296, 10 pages.

* cited by examiner

APPARATUS AND SYSTEMS FOR POWERING SUPPORTS FOR EXOSKELETONS

CROSS REFERENCE TO RELATED APPLICATIONS

This application is a 35 U.S.C. § 371 national stage entry of PCT/IL2016/051296, entitled "Apparatus and Systems for Powering Supports for Exoskeletons," filed Dec. 4, 2016, which in turn claims priority to U.S. Provisional Patent Application No. 62/263,468, entitled "Apparatus and Systems for Powering Supports for Exoskeletons," filed Dec. 4, 20151. The disclosure of each of the above applications is incorporated by reference herein in its entirety.

FIELD OF THE DISCLOSURE

Embodiments of the current disclosure are directed toward mobility supports for providing gait/movement assistance, and more particularly, methods and apparatus for powering smart crutches that include electronic circuitry.

BACKGROUND OF THE FIELD OF THE DISCLOSURE

Various conditions contribute to the occurrence of disabilities in individuals that restrict or eliminate the individuals' capabilities for steady gait and/or movement, examples of which include neurological and physical injuries. Exoskeletons ("external skeletons") and supports such as crutches have been used to allow such individuals regain some or all of their capabilities to stand and/or move about with little or no additional support despite their disabilities.

SUMMARY OF SOME OF THE EMBODIMENTS

Some embodiments of the disclosure provide a smart crutch charging apparatus which comprises a base unit configured to supply a recharging voltage and current, at least one crutch receiving portion arranged on or within the base unit, at least one base terminal arranged within, thereon and/or proximate to each of the at least one crutch receiving portions, where upon at least a portion of a smart-crutch being received by, in and/or on the crutch receiving portion:

the at least one base terminal is configured to electrically or magnetically couple with a corresponding crutch terminal of the at least a portion of the smart-crutch, and the base unit supplies the recharging voltage and current to the smart-crutch so as to recharge a rechargeable power supply contained in/on the smart-crutch.

Such embodiments may further include one and/or another of the following features:

the base unit is configured as a free-standing structure for placement on a horizontal surface;

at least a portion of the smart-crutch comprises a distal end of a smart-crutch, and the at least one crutch receiving portion is configured to receive the distal end of a smart-crutch;

a stabilization means configured for retaining at least one smart-crutch in an upright position upon the at least a portion of the smart-crutch being received by, in and/or on the receiving portion;

the base unit is configured as a wall-mounted unit;

the crutch receiving portion comprises a mounting clamp configured with an opening for receiving the at least a portion of smart-crutch;

the clamp is configurable in an open and a closed position, where in the open position, the opening is configured to receive the at least one portion of the smart-crutch, and in the closed position: the at least one smart-crutch is retained by the clamp; and/or the base terminal comes into contact and/or proximity to the crutch terminal;

each of the base terminal and crutch terminal are configured to physically contact one another upon the at least a portion of the smart-crutch being received by, in and/or on the at least one receiving portion;

each of the base terminal and crutch terminal are configured as independent coils arranged proximate one another and configured to recharge the rechargeable power supply of the smart-crutch via inductive charging upon the at least a portion of the smart-crutch being received by, in and/or on the at least one receiving portion;

at least one conducting element, where at least a portion of the at least one conducting element is arranged by, in and/or on the at least one crutch receiving portion;

the conducting element comprises an magnetic core;

a transformer configured to convert alternating-current (AC) received from a source of AC to direct-current (DC) for supplying the voltage and current to recharge at least one smart-crutch;

a power supply cable configured to electrically connect the apparatus to a source of AC power;

a sensor, which may be selected from the group consisting of: a pressure sensor, a proximity sensor, and a power level sensor for sensing a power level of the rechargeable energy source, and any combination of the foregoing;

a communications unit configured for communicating at least one of a smart-crutch, a computing device/system, and an exo-skeleton/soft-exosuit apparatus; and a diode-bridge configured to harmonize polarities of the base terminal and the crutch terminal.

In some embodiments, a smart-crutch charging system is provided which may comprise at least one smart-crutch charging apparatus according to any of the disclosed embodiments, and at least one smart-crutch.

In some embodiments, a smart-crutch charging system is provided which comprises at least one smart-crutch charging apparatus according to any of the disclosed embodiments, at least one smart-crutch; and an exo-skeleton/exo-suit apparatus.

Some embodiments of the current disclosure also include a method comprising the steps of: configuring a base unit to supply a recharging voltage and current; arranging at least one crutch receiving portion on or within the base unit; and arranging at least one base terminal within, thereon and/or proximate to each of the at least one crutch receiving portion. In some embodiments, upon at least a portion of a smart-crutch being received by, in and/or on the crutch receiving portion: the at least one base terminal is configured to electrically or magnetically couple with a corresponding crutch terminal of the at least a portion of the smart-crutch, and the base unit supplies the recharging voltage and current to the smart-crutch so as to recharge a rechargeable power supply contained in/on the smart-crutch.

In some embodiments, the step of configuring the base unit to supply a recharging voltage and current includes arranging the base unit as a free-standing structure for placement on a horizontal surface. In some embodiments, configuring the base unit to supply a recharging voltage and current includes arranging the base unit as a wall-mounted unit.

Further, the method may comprise providing a stabilization means configured for retaining at least one smart-crutch in an upright position upon the at least a portion of the smart-crutch being received by, in and/or on the receiving portion. In addition, the method may comprise providing a transformer configured to convert alternating-current (AC) received from a source of AC to direct-current (DC) for supplying the voltage and current to recharge at least one smart-crutch. The method may also include the step of configuring a communications unit to communicate at least one of a smart-crutch, a computing device/system, and an exo-skeleton apparatus. Further, the method may comprise providing the smart-crutch and/or an exoskeleton apparatus.

In some embodiments, each of the base terminal and crutch terminal are configured to physically contact one another upon the at least a portion of the smart-crutch being received by, in and/or on the at least one receiving portion. In some embodiments, each of the base terminal and crutch terminal are configured as independent coils arranged proximate one another and configured to recharge the rechargeable power supply of the smart-crutch via inductive charging upon the at least a portion of the smart-crutch being received by, in and/or on the at least one receiving portion.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION OF SOME OF THE EMBODIMENTS

Figure 1:
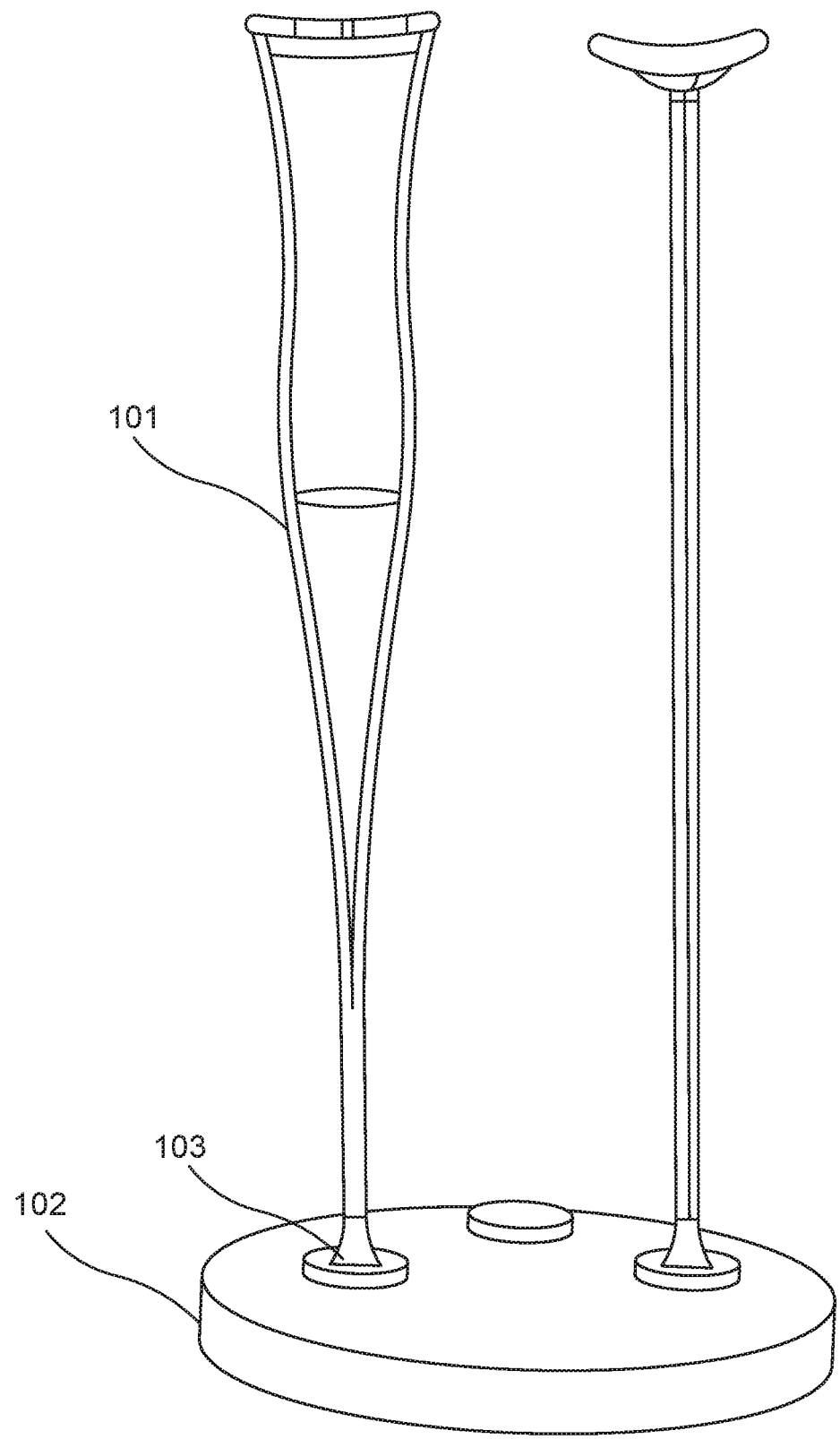
FIG. 1 shows example embodiments of smart crutches configured for charging via a floor charger.

In some embodiments of the present disclosure, methods, apparatus and systems for providing gait/movement assistance, and more particularly, methods, apparatus and systems for powering smart crutches that include electronic circuitry are presented. Although amenable to various applications, specific embodiments are described herein, by way of example and not limitation, in order to illustrate the principles and features of the invention.

In some embodiments, the smart crutches may be crutches that include electronic circuitry. The electronic circuitry may include any electronic component such as, but not limited to, lighting sources (e.g., flashing light, etc.), sensors (e.g., sensors for sensing pressure, motion, orientation, direction, tilt, location, elevation, temperature, voltage, current etc.), processing units, communications modules (e.g., wireless), power sources (e.g., batteries) and/or the like. These components allow the crutches to collect and log data, and process and/or transmit the collected and/or processed data to other crutches and external devices such as smartphones, servers, exoskeletons, and the like. Further, the components may be configured to receive data and/or instructions from the external devices (e.g., wirelessly). Various aspects of the smart crutches and the exoskeleton device, and interactions therebetween have been described in the following publications, all of which are incorporated by reference herein in their entireties:

U.S. Provisional Patent Application No. 62/242,780, filed Oct. 16, 2015, and entitled "Apparatus and Systems for Controlling Exoskeletons;"

PCT International Patent Application No. PCT/IL2016/051125, filed Oct. 16, 2016, and entitled "Apparatus and Systems for Controlling Exoskeletons;"

U.S. Provisional Patent Application No. 62/189,148, filed Jul. 6, 2015, and entitled "Methods and Apparatuses for Exoskeleton Attachment;"

U.S. Pat. No. 7,153,242, issued Dec. 26, 2006, filed May 24, 2001, and entitled "Gait-locomotor apparatus;"

U.S. Pat. No. 8,905,955, issued Dec. 9, 2014, filed Jan. 7, 2013, and entitled "Locomotion assisting device and method;"

US Patent Publication No. 2012/0101415, published Apr. 26, 2012, filed Oct. 21, 2010, and entitled "Locomotion Assisting Apparatus with Integrated Tilt Sensor;"

US Patent Publication No. 2013/0253385, published Sep. 26, 2013, filed Mar. 21, 2012, and entitled "Motorized Exoskeleton Unit;"

US Patent Publication No. 2014/0005577, published Jan. 2, 2014, filed Jun. 28, 2012, and entitled "Airbag for Exoskeleton Device;" and US Patent Publication No. 2014/0196757, published Jul. 17, 2014, filed Jan. 17, 2013, and entitled "Gait Device with a Crutch."

In some embodiments, the noted electronic circuitry may be powered by an energy source that is rechargeable and/or replaceable. In some cases, these energy sources can be self-contained modules such as batteries, examples of which include, lithium ion batteries, alkaline batteries, nickel metal or nickel cadmium batteries, lead acid batteries, organic or non-organic supercapacitors, fuel cells, so-called smart batteries. In some embodiments, the energy sources may be integrated into the crutches effectively permanently, and may not be at least routinely removable (e.g., their removal from a crutch may be accompanied by severe damage to a host crutch). In such embodiments, the energy sources may be rechargeable (e.g., without being removed from the crutch). In some embodiments, the energy sources may be removable/replaceable. In some embodiments, such replaceable or disposable energy sources may not be chargeable (e.g., they may be single-use types) and may have to be replaced once they are depleted.

In some embodiments, removable chargeable energy sources can be recharged with or without being removed from the host crutch. In some embodiments, the crutch may be configured to provide a convenient access to the rechargeable energy sources so as to facilitate the charging of the energy sources by an external charging mechanism and/or the powering of the electrical components of the crutch. For example, the rechargeable energy sources can be recharged without necessarily being detached from the crutches the energy sources are powering. In such embodiments where the energy sources may not have to be removed for charging, manufacturing and other constraints associated with having an access for removing an energy source, which usually tend to increase the cost and complexity of the design and construction of the crutches, may not be present. Whether removable or not, the rechargeable sources can be recharged while still being attached to the crutches (e.g., residing within the crutches). Some of the disclosed embodiments of the present disclosure discuss apparatus, methods and system of powering smart crutches and the energy sources that support them. Non-limiting examples of such embodiments include a wired and/or wireless floor charger, a wired and/or wireless wall charger, and a portable charger (e.g., travel charger).

With reference to FIG. 1, in some embodiments, a floor charger 102 for charging a smart crutch 101 wirelessly and/or via a wired connection is shown. The floor charger may comprise an AC-DC transformer circuit for transporting, altering and/or converting an alternating current (AC) power source into a direct current (DC) power source that can be used for charging a rechargeable energy source of the crutch (which may be a removable or non-removable part of the crutch) and/or powering electrical components of the mobility devices. Non-limiting examples of the rechargeable energy source include one or more of the battery types disclosed above. The charger 102 may be a base unit configured to receive the distal end of a smart crutch 101 and provide stability to the smart crutch 101 such that the smart crutch can remain coupled to the charger 102 in a stable manner (e.g., stay substantially upright when engaged with the charger 102). For example, the charger 102 may include stability locks 103 that keep or lock in the crutch 101 in a standing position when the crutch 101 is inserted into the charger. In some embodiments, another section of a crutch, instead of or in addition to the distal end of the crutch, may be used in charging the energy sources of the crutch and/or powering the electrical sources of the crutch. Such a section, however, may be configured to couple to or be received by the floor charger 102 so as to facilitate the charging/powering process. While not being charged or powered, the floor charger 102 may also be used to store the smart crutch 101. As such, the base unit or charger 102 is configured to be a free-standing structure for placement on a horizontal surface and capable of providing support to the smart crutches. In some embodiments, the charger 102 may include a switch (not shown) that allows users to commence or interrupt the charging process.

The floor charger 102 may be designed so as to have any shape and form so long as it is capable of receiving a distal or any other designated end of the smart crutch 101 for charging and/or powering the crutch (e.g., by charging batteries contained within the crutch). For example, the floor charger 102 may be part of a home's décor (e.g., part of a home's floor, furniture, etc.) or it can be a separate module containing the above-noted components such as the transformer and the AC-DC adapter). In any case, the floor charger 102 may be configured to receive a distal end of the crutch 101 and allow the transfer of energy to the crutch. The distal end of the crutches 101 may include both positive and negative terminals for contact with the receiving terminals (positive and negative as well, for example) of the floor charger 102. In some embodiments, the distal end may be covered with a shield such as rubber. Although the current disclosure discusses the distal end of the crutch as the part of the crutch that is being received by the charger 102, it is to be understood that all the embodiments of the disclosure also apply to any other section of the crutch 101 that is configured to being received by the charger 102 so as to facilitate the charging of the energy or power sources of the smart crutch 101.

In some embodiments, the floor charger 102 may comprise sensors for detecting and/or monitoring various states of the charger itself, of crutches being powered up, environmental conditions, etc. For example, the floor charger may comprise a power sensor (not shown) that monitors when a smart crutch 101 is charging, and provide feedback about the charging process. For example, the power sensor may detect whether the performance of the charging process has degraded (e.g., due to foreign objects short circuiting, increasing electrical resistance or obstructing the contact between the crutch 101 and the floor charger 102). Another reason for the degradation of the charging process can be the possible degradation or defectiveness of the energy source of the crutch 101 itself. Indications (and measures thereof) of the conditions of the charging process, and by extension the energy source of the crutch 101, and/or the contact between the crutch 101 and the charger 102, may be determined from the rate of energy transfer from the charger 102 to the crutch 101. The power sensor may also determine the amount of energy available (or depleted) in the energy source of the smart crutch 101 (e.g., by measuring the percentage of power remaining in a battery in the smart crutch). In some embodiments, the power sensor may also determine the amount of time that may be needed to charge the power source of the crutch 101 fully or to some determined power level. For example, the power sensor may determine, based on the rate of charging, the amount of charge remaining in a crutch's energy or power source, etc., the amount of time the crutch 101 needs to charge for the energy or power source to attain at a determined power level.

The floor charger 102 may also include other types of sensors, such as a temperature sensor to detect the internal temperatures of the floor charger, the contact with the crutch and/or the surrounding environment (i.e., ambient temperature), a contact sensor (e.g., pressure sensor) for determining whether the smart crutch 101 is appropriately connected to the floor charger 102, a proximity detector for detecting correct insertion of smart crutch into the receiving charger 102 (for use, for example, in facilitating the enabling/disabling of charging for safety reasons). In some embodiments, the floor charger 102 may also include a communications unit (e.g., comprises a wireless module) for transmitting the sensed or any other gathered data to/from crutches, external servers (e.g., smartphones, etc.), exoskeletons etc. Examples of such data include the amount of power remaining in the power source of the crutch 101, the length of time it would take to charge the power source to the desired power level (as determined by the power sensor, for example), the efficiency of the charger in charging the power source (for example, as determined from the charging rate) and/or powering the electrical components of the crutch, and/or the like. In such embodiments, the communications unit may also be configured to receive incoming data. Examples of incoming data include instructions from external devices to activate or deactivate the charging of the power source of the crutch 101, to set or modify charging settings (e.g., the time duration for charging the power source, the power level the power source should be charged to (e.g., 100%, 75%, 50%, etc.), and/or the like. In some embodiments, such instructions may then be transmitted to a processing circuitry for further processing as discussed below with respect to certain embodiments. An additional application of the communications unit can be facilitating the capability to initiate crutch search when the crutch is not placed on the charger (e.g., location function to locate a crutch via, for example, an audible alarm). For example, the charger 102 and the crutch 101 may be configured to communicate with each other (e.g., via anyone of wireless communication technologies such as RFID, WiFi, and/or the like), a switch on the charger 102 may allow a user to activate an audible and/or visible alarm on the crutch (e.g., via messages sent by the charger's communications unit to a corresponding one at the smart crutch 101) to aid in locating the crutch. In some embodiments, the charger 102 may be configured to generate an alarm (e.g., sound, visual, etc.) whenever the smart crutch energy is depleted (as detected by the power sensor, for example) below the preprogrammed or adaptable threshold so that the charging of the crutch's power source and/or the powering of the crutch is commenced (by a user, for example).

In some embodiments, the floor charger 102 may also include a processing unit for processing the gathered and/or received data. For example, the power sensor may detect the level of power available in the energy source of the crutch 101, and the processing unit, based at least partially on the detected data from the power sensor, may calculate the amount of time that would be required to charge the energy source to full capacity. As another example, the processing unit may receive data from the proximity detector, and determine correctness of the insertion of smart crutch distal. Further, based on one or more of the sensed or received data such as the temperatures of the charger 102 and/or the crutch 101, the charging rate of the power source, etc., the processing unit may determined the efficiency of the charging process (i.e., whether the charger has degraded or not). Upon making such determinations, in some embodiments, the processing unit may then cause the activation of various segments of the charger 102 (e.g., activate the charging of the crutch 101 when determining the power level is below a threshold amount) or facilitate the transmission of such determinations (e.g., via the communications unit) to external devices such as exoskeletons, smartphones, etc.

In some embodiments, the communications unit of the floor charger 102 may be configured to communicate any data, including information gathered by the various sensors and/or data generated by the processing unit. For example, as mentioned above, the communications unit may transmit and/or receive data to crutches, external servers, exoskeletons (e.g., the exoskeleton a smart crutch is associated with), etc. Other forms of communication include visual (e.g., lights), audio, etc. For example, the communications unit may include a user interface and may display in the interface the state of the floor charger (e.g., on, off, sleep, etc.), the power level of the energy source of the crutch 101 (e.g., percentage of power available or missing), time duration for charging the crutch power source and/or time duration left before the power level attains some determined value (e.g., as supplied by a clock associated with or contained within the floor charger), temperature, etc. Similar information may also be supplied via audio outputs. For example, a beeping alarm sound may indicate that a foreign object has interfered with the terminals of the floor charger where the smart crutch is configured to be contacted. In some embodiments, the communication unit may also include a user interface for receiving input data from users. For example, the user interface may include a switch for activating and deactivating the floor charger or a switch for locating a crutch as discussed above. The interface may also be configured to receive the above-noted instructions that may include input data such as amount of charging time and/or the like.

Figure 2:
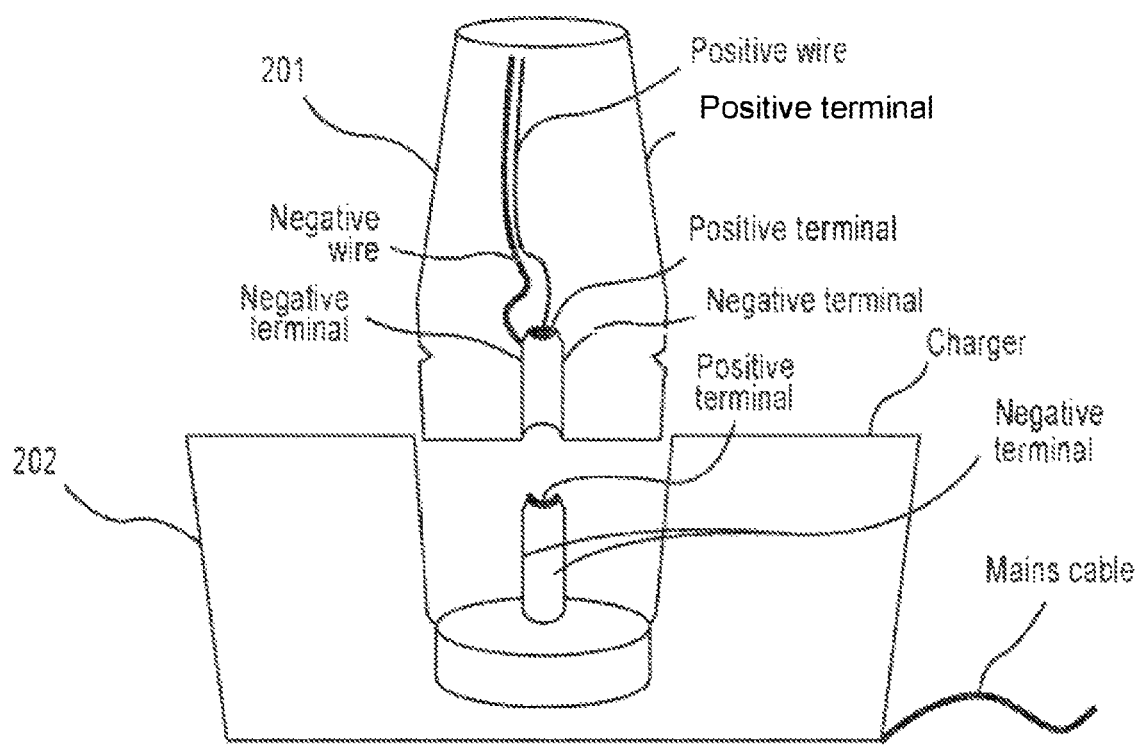
FIG. 2 shows an example embodiment of a terminal alignment between a distal end of a crutch and a floor charger configured for receiving the distal end in a wired charging arrangement.

With reference to FIG. 2, in some embodiments, a floor charger 202 configured for receiving the distal ends of crutches 201 in a wired charging arrangement is shown. In such embodiments, "wired" refers to the fact that the terminals on the crutches are in galvanic contact with terminals on the charger and the transfer of power between the floor charger and the crutches is facilitated by a direct electrical contact. The floor charger 202 may include an AC/DC converter for transforming an incoming AC voltage into a DC voltage that can be used for charging rechargeable energy sources and/or powering crutches. The amount of the DC voltage may depend on the power requirements of the crutches to be powered as well as other considerations such as safety reasons and efficiency. For example, the amount of the DC voltage may be chosen so as not to exceed an appropriate electrical safety rating above which exposure to the terminals of the floor chargers and/or the smart crutches can be dangerous to humans and animals (e.g., no more than 60V DC). In some cases, the floor charger 202 may be designed so as to shield the terminals from exposure while still allowing contact and transfer of charging energy between the floor charger and crutches. For example, a removable or fixed (i.e., permanent) cover can provide mechanical protection to the terminals of the floor chargers and/or the smart crutches while providing an access point for a portion of the crutch 201 to make electrical contact with the charger 202. For example, the charger 202 may include an opening for the distal ends of crutches 201 to be inserted and make contact with the terminals. Further, the opening may assume a shape or pattern that matches the shape of the distal ends of crutches, allowing the distal end to effectively function as also a key that unlocks the mechanical protection. An opening with a unique pattern, for example, may effectively be used as a gate keeper that keeps most other objects out while allowing crutches with matching distal ends enter the floor charger and make contact with the terminals.

In some embodiments, one of the major advantages of wired charging may be the high efficiency of power transfer between the floor charger and the crutches (e.g., above about 90%, about 95%, about 98%, etc.). The high efficiency can be at least partially the result of the relatively low electrical resistance of wires in carrying and transferring the DC current provided by the floor charger. In addition, the direct contact between the terminals of the floor charger and the smart crutch may facilitate the said high efficiency. However, there may be disadvantages that come from having direct contact between the crutches and the floor charger, including the fact that for direct contact to take place, there may have to be at least a small opening (as discussed above, for example) exposing the terminals to moisture, dust and in general contaminants that disrupt and degrade the transfer of power from the charger to the crutches. In order to offset these disadvantages a mechanical protection approach may be implemented. For example, as explained above, an opening with a unique pattern that can be unlocked only by distal ends of a crutch having a matching pattern may provide such mechanical protections.

Figures 3A, 3B:
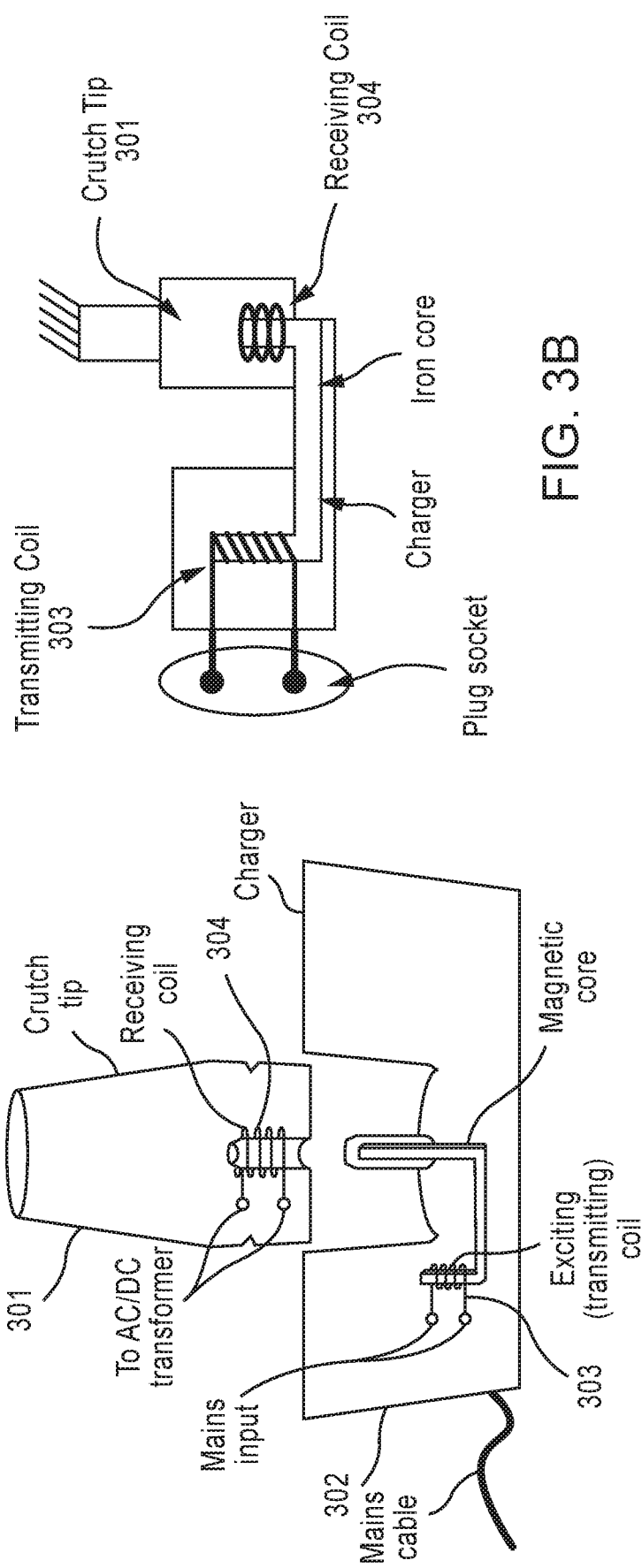
FIG. 3A shows an example embodiment of a terminal alignment between a distal end of a crutch and a floor charger configured for receiving the distal end in a wireless charging arrangement.
FIG. 3B shows an example schematic illustration of coupling of a crutch's distal end to a magnetic core of a charger, according to some embodiments.

With reference to FIG. 3, in some embodiments, the charging of crutches can be accomplished wirelessly by a transformer, which can be used to transfer electrical energy from the floor charger 302 to the crutches via electromagnetic induction (which may include, for example, a power transfer efficiency in the range from about 50% to about 80%, from about 55% to about 75%, from about 60 to about 75%, etc.). For example, an AC signal (e.g., transformed AC power from a standard wall outlet) may be used to excite a transmitting coil disposed within a floor charger 302. That is, the mains cable may initiate an AC in the transmitting coil that in turn may induce a changing magnetic field within the floor charger 302. For example, the transmitting (primary) coil 303 may be wound around a magnetic element such as an iron core disposed within the floor charger 302, and the AC excited in the transmitting coil may induce a changing magnetic field. However, a changing magnetic field is known to induce an AC voltage in a coil wound around the conductive element. As such, the induced, changing magnetic field may be used to induce an AC voltage in the crutches by "conveying" the changing magnetic field from the floor charger 302 to the crutches and inducing an AC voltage in a receiving (secondary) coil located in the distal end 304 of the crutches. In such embodiments, AC voltage can be induced in the receiving coil 304 when the distal end 301 of the smart crutch enters into a recess of the floor charger 302, which results in the receiving coil 304 being wound around the magnetic element, as shown in FIGS. 3A and 3B. FIG. 3B shows a schematic illustration of the coupling of the distal end or tip 301 of the crutch to the charger 302. In such embodiments, the crutches may include an AC/DC transformer that can be used to convert the induced AC voltage in the receiving coil into a DC power that can be used to charge rechargeable energy sources and/or power components of the crutches. In some of these cases, there may not be an AC/DC transformer in the floor charger.

Besides the aforementioned power transformer which uses inductive coupling between a pair of coils to transfer power, in some embodiments, there may be other techniques for wirelessly transferring power between the floor charger and the crutches. For example, planar coils may be used for such applications. Other examples may use other types of coupling including capacitive coupling (energy transform via electric field charging secondary electrode from the primary), magneto-dynamic coupling (energy transfer from primary to secondary coil without magnetic core), etc.

In contrast to wired charging systems, for wirelessly charging systems, the terminals of the floor charger and/or the crutch may be sealed to isolate the terminals from the surrounding environment and protect their ability to convey energy and their integrity. For example, the seals may protect the terminals from moisture, liquid, dust, extraneous objects, etc., that would otherwise interfere and/or short-circuit the connections.

The wired and wireless charging systems of FIG. 2 and FIGS. 3A-B are described above with respect to the embodiments of the floor charger, shown in FIG. 1, for example. However, in addition to or in place of a floor charger, the wired and wireless charging systems of the present disclosure can be realized in different forms. For example, the noted charging systems can be realized as wall chargers. This may be advantageous from practical considerations such as convenience for a user (in particular disabled user), compact storage, etc. All the features of the floor charger discussed above may apply equally to wall chargers, except for the distinctions as discussed below. For example, the wall charger may comprise the above discussed sensors, processing unit, communications unit, and/or the like.

In realizing the wired and wireless charging systems as wall chargers, there may be some differences that arise that may be unique to wall charging, or at least more pronounced in the case of wall charging. For example, the ways of mounting the crutches to the base charger (located on the wall as opposed to the floor charger above) and the placement of the terminals on the crutches are issues that have to be considered. Any type of mounting method that could stably hold the crutches in place as long as needed so as to allow the charging of the crutches from a wall charger located in a wall can be used for realizing a wall charging mechanism. For example, a "claw" or clamp type mount can be used to mount crutches to a wall charger. The mount may also have additional features that enhance convenience, safety, etc. For example, the clamp may be configured to automatically open and/or close whenever a smart crutch is inserted and/or about to be inserted into the clamp so as to establish contact between the crutch and the wall charger. This may be accomplished by a proximity sensor in the wall charger, the wall, the clamp, and/or the smart crutch that senses closeness of the smart crutch to the clamp/wall charger, for example. In some embodiments, the closing of the clamp may be effected whenever any appropriately shaped object (e.g., cylindrical body with matching diameter as that of the clamp) is inserted in the clamp. In any of these wall mounting embodiments, the release of a mounted crutch may be accomplished via any number of methods, including application of force (e.g., manual clamp), a release button (e.g., with mechanical button located in the vicinity of the clamp), in an automatic fashion as described above (e.g., a proximity sensor senses movement of the smart crutch and facilitates the opening of the clamp) and a combination of above methods, etc.

In some embodiments, the clamps may also be used for the purposes of terminal placement for the wall charger. For example, the clamp may comprise one or more stripes of power terminals that can come into contact with a smart crutch when the crutch is mounted on the wall. In most cases, these stripes may be located on the inside ring of clamps for safety reasons, to allow firm contact between the terminals of the clamp (effectively the wall charger) and the crutches, and/or the like. There may be a plurality of stripes, and the stripes may represent a combination of positive and negative terminals. For example, the terminals can be a plurality of conducting stripes (e.g., metals) isolated from one another via a non-conducting spacer.

In such embodiments, the terminals on crutches may be configured so as to allow an efficient transfer of power between the wall charger and the crutches when the crutches are mounted on the wall. The terminal stripes on the clamps and/or the crutches may be organized such that regardless of the way a smart crutch is mounted on the wall or inserted into the clamp, power terminal stripes on the crutches come into contact with matching stripes on the charger clamp. For example, a diode bridge (e.g., disposed in crutches) may be used to facilitate the transfer of power between the wall charger and the crutches whenever stripes on the clamp and the crutches come in contact regardless of polarity (i.e., polarity of the mating stripes may become non-relevant as the diode bridge can allow the smart crutch to receive the energy regardless the input polarity. This can be accomplished because diode bridges provide same polarity of output for either polarity of input, and whatever two stripes come in contact, the power is transferred with right polarity. Additional non conducting stripes or spacers may be introduced between conducting ones on the crutches so as to avoid short circuiting and further match the arrangement of terminal stripes on the clamp charger. In some embodiments, the transferring of the power (e.g., amount, rate, etc.) may be designed with safety considerations in mind. For example, the transferred power may have low enough voltage so as not to cause damage to a human or animal that may come into contact with the terminals during a charging process. In some embodiments, the proximity detector may be used to sense an approach or touch by a subject so as to suspend the charging until further indications are received by the wall charger to resume charging. For example, similar to the discussion above with respect to the floor charger, the wall charger may comprise a user interface for receiving input from users. In this example, a user may input instructions allowing the charging process to continue, in some cases including specifications for settings such as the duration of the charging, the power level to be charged to, etc. In some embodiments, a protective cover may be placed over the exposed terminals before or after the mounting of the crutches.

Figure 4B:
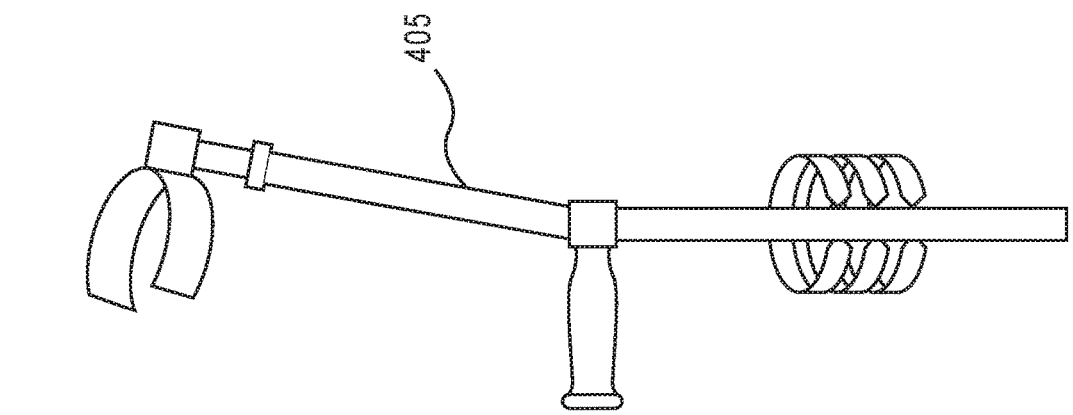
FIGS. 4A-B show example embodiment of a wireless charging mechanism for a wall mounted charger.
Figure 4A:
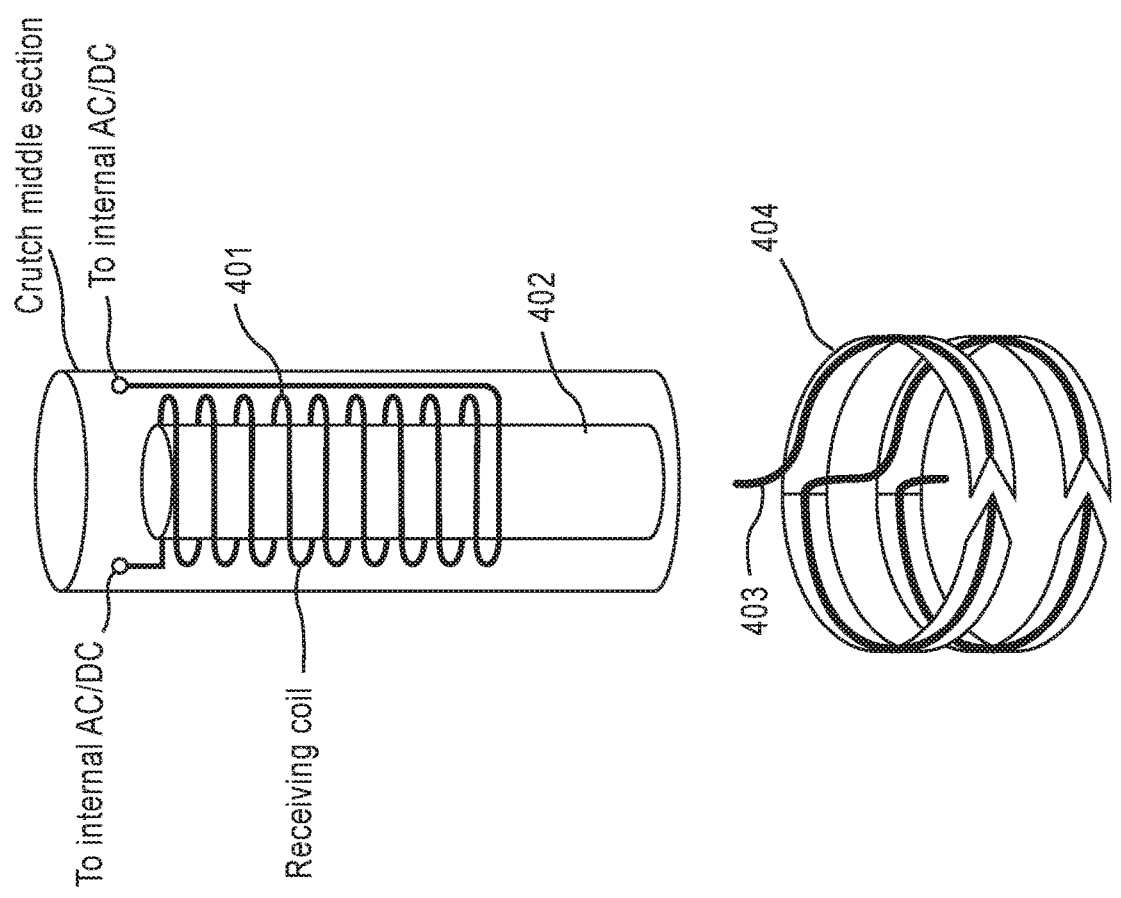

With reference to FIGS. 4A-B, in some embodiments, a wireless charging mechanism for a wall mounted charger is shown. The mechanism can include several features of FIG. 3, which is directed to a floor charging system, but adapted to a wall charging system. Using a non-limiting cylindrical-shaped set up for the crutches, FIG. 4A shows the receiving coil 401 and the magnetic element 402 (e.g., an iron core) disposed or embedded within the body of the crutches. The transmitting or exiting coil 403 can be disposed in the charging "clamp" 404 used to restrict and hold the crutches. The stripes of the clamp may include conduction materials and may have spiral structure. In some embodiments, the closing of the clamp upon insertion of a crutch may form or complete the transmitting coil and initiates the charging process. As a particular example embodiment, the closing of the charging clamp 404 shown in FIG. 4A may commence the charging of the crutch 405 when the crutch 405 is inserted and surrounded by the clamp 404. in some embodiments, similar to the discussion provided above with reference to the floor charger (FIGS. 3A-B), the magnetic element may "convey" magnetic energy towards the receiving core inside the crutches, which can induce AC voltage in the receiving coil. An AC-DC transformer may then be used to transform the AC power signal into DC for charging the rechargeable energy source or powering the electrical components within the crutches.

In some embodiments, a mobile charging system may be realized by using a portable power source instead of a "walled" power source. For example, all the features of the wall charger may be incorporated into this portable charging system where the mounting interface may be via a cable rather than a wall. For example, the clamps type terminal may be attached to power cable configured to receiving power from wall AC adapter/charger or it can be fixed on the power cable connected to exoskeleton itself. The later example does not require AC/DC transformer since the exoskeleton is normally powered by DC power source. In such embodiments, the crutches may be charged from the mains brick charger or from the exoskeleton associated with the crutches. In some embodiments, the floor charger as well as the wall charger discussed above may be implemented so as to be a portable power source for charging the power source of the crutch and/or powering the electrical components of the crutch. For example, the floor charger and/or the wall charger may be equipped with a power source of their own. In some embodiments, the floor charger and/or the wall charger may be coupled to another structure or device, such as an exoskeleton, that may have access to either DC or AC power.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Still further, some embodiments disclosed herein are distinguishable over prior art references by specifically lacking one or more features disclosed in the prior art; that is, claims to such embodiments may include negative limitations so as to be distinguished from the prior art.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various implementations of some of embodiments disclosed, in particular at least some of the processes discussed (or portions thereof), may be realized in digital electronic circuitry, integrated circuitry, specially configured ASICs (application specific integrated circuits), computer hardware, firmware, software, and/or combinations thereof. These various implementations, such as associated with the controller 254, for example, may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Such computer programs (also known as programs, software, software applications or code) include machine instructions/code for a programmable processor, for example, and may be implemented in a high-level procedural and/or object-oriented programming language, and/or in assembly/machine language. As used herein, the term "machine-readable medium" refers to any computer program product, apparatus and/or device (e.g., non-transitory mediums including, for example, magnetic discs, optical disks, flash memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a LCD (liquid crystal display) monitor and the like) for displaying information to the user and a keyboard and/or a pointing device (e.g., a mouse or a trackball, touchscreen) by which the user may provide input to the computer. For example, this program can be stored, executed and operated by the dispensing unit, remote control, PC, laptop, smart-phone, media player or personal data assistant ("PDA"). Other kinds of devices may be used to provide for interaction with a user as well. For example, feedback provided to the user may be any form of sensory feedback (e.g., visual feedback, auditory feedback, or tactile feedback), and input from the user may be received in any form, including acoustic, speech, or tactile input. Certain embodiments of the subject matter described herein may be implemented in a computing system and/or devices that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components.

The components of the system may be interconnected by any form or medium of digital data communication (e.g., a communication network). Examples of communication networks include a local area network ("LAN"), a wide area network ("WAN"), and the Internet. The computing system according to some such embodiments described above may include clients and servers. A client and server are generally remote from each other and typically interact through a communication network. The relationship of client and server arises by virtue of computer programs running on the respective computers and having a client-server relationship to each other.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A smart crutch charging apparatus comprising:
a base unit configured to supply a recharging voltage and current;
at least one crutch receiving portion arranged on or within the base unit;
at least one base terminal arranged within, thereon and/or proximate to each of the at least one crutch receiving portion,
wherein:
upon at least a portion of a smart-crutch being received by, in and/or on the crutch receiving portion:
the at least one base terminal is configured to electrically or magnetically couple with a corresponding crutch terminal of the at least a portion of the smart-crutch,
and
the base unit supplies the recharging voltage and current to the smart-crutch so as to recharge a rechargeable power supply contained in/on the smart-crutch,
the base unit is configured as a wall-mounted unit, and
the crutch receiving portion comprises a mounting clamp configured with an opening for receiving the at least a portion of the smart-crutch.

2. The apparatus of claim 1, wherein the base unit is configured as a free-standing structure for placement on a horizontal surface.

3. The apparatus of claim 2, wherein at least a portion of the smart-crutch comprises a distal end of a smart-crutch, and wherein the at least one crutch receiving portion is configured to receive the distal end of a smart-crutch.

4. The apparatus of claim 1, further comprising a stabilization means configured for retaining at least one smart-crutch in an upright position upon the at least a portion of the smart-crutch being received by, in and/or on the receiving portion.

5. The apparatus of claim 1, wherein:
the clamp is configurable in an open and a closed position,
in the open position, the opening is configured to receive the at least one portion of the smart-crutch,
and
in the closed position: the at least one smart-crutch is retained by the clamp, and/or the base terminal comes into contact and/or proximity to the crutch terminal.

6. The apparatus of claim 1, wherein each of the base terminal and crutch terminal are configured to physically contact one another upon the at least a portion of the smart-crutch being received by, in and/or on the at least one receiving portion.

7. The apparatus of claim 1, wherein each of the base terminal and crutch terminal are configured as independent coils arranged proximate one another and configured to recharge the rechargeable power supply of the smart-crutch via inductive charging upon the at least a portion of the smart-crutch being received by, in and/or on the at least one receiving portion.

8. The apparatus according to claim 7, further comprising at least one conducting element, wherein at least a portion of the at least one conducting element is arranged by, in and/or on the at least one crutch receiving portion.

9. The apparatus of claim 8, wherein the conducting element comprises a magnetic core.

10. The apparatus of claim 1, further comprising a transformer configured to convert alternating-current (AC) received from a source of AC to direct-current (DC) for supplying the voltage and current to recharge at least one smart-crutch.

11. The apparatus of claim 1, further comprising a power supply cable configured to electrically connect the apparatus to a source of AC power.

12. The apparatus of claim 1, further comprising a sensor.

13. The apparatus of claim 12, wherein the sensor is selected from the group consisting of: a pressure sensor, a proximity sensor, and a power level sensor for sensing a power level of the rechargeable energy source, and any combination of the foregoing.

14. The apparatus of claim 1, further comprising a communications unit configured for communicating with at least one of a smart-crutch, a computing device/system, and an exo-skeleton apparatus.

15. The apparatus of claim 1, further comprising a diode-bridge configured to harmonize polarities of the base terminal and the crutch terminal.

16. A smart-crutch charging system comprising:
at least one smart-crutch charging apparatus according to claim 1;
and
at least one smart-crutch.

17. A smart-crutch charging system comprising:
at least one smart-crutch charging apparatus according to claim 1;
at least one smart-crutch; and
an exo-skeleton apparatus.

* * * * *